United States Patent
Bauerfeind et al.

(10) Patent No.: US 6,994,682 B2
(45) Date of Patent: Feb. 7, 2006

(54) KNEE-JOINT ORTHESIS

(75) Inventors: Hans B Bauerfeind, Zeulenroda (DE); Holger Reinhardt, Kempen (DE); Rainer Scheuermann, Raisdorf (DE)

(73) Assignee: Bauerfeind AG, (DE)

( * ) Notice: Subject to any disclaimer, the term of this patent is extended or adjusted under 35 U.S.C. 154(b) by 0 days.

(21) Appl. No.: 10/488,285

(22) PCT Filed: Sep. 3, 2002

(86) PCT No.: PCT/EP02/09841

§ 371 (c)(1),
(2), (4) Date: Aug. 24, 2004

(87) PCT Pub. No.: WO03/020187

PCT Pub. Date: Mar. 13, 2003

(65) Prior Publication Data

US 2005/0004499 A1  Jan. 6, 2005

(30) Foreign Application Priority Data

Sep. 3, 2001 (DE) ................................ 101 43 067

(51) Int. Cl.
*A61F 5/00* (2006.01)
(52) U.S. Cl. .............................. 602/26; 602/13; 602/16
(58) Field of Classification Search .................. 602/16, 602/27, 26, 23, 5, 13; 128/DIG. 20
See application file for complete search history.

(56) References Cited

U.S. PATENT DOCUMENTS

| | | | |
|---|---|---|---|
| 4,219,892 A * | 9/1980 | Rigdon ............................. 2/24 |
| 4,556,053 A * | 12/1985 | Irons ............................ 602/26 |
| 4,643,176 A * | 2/1987 | Mason et al. ................... 602/16 |
| 4,796,610 A | 1/1989 | Cromartie |
| 4,940,045 A * | 7/1990 | Cromartie ..................... 602/16 |
| 5,302,169 A | 4/1994 | Taylor |
| 5,360,394 A * | 11/1994 | Christensen .................. 602/26 |
| 5,415,625 A | 5/1995 | Cassford et al. |
| 5,520,622 A * | 5/1996 | Bastyr et al. .................. 602/16 |
| 5,588,956 A * | 12/1996 | Billotti ......................... 602/13 |
| 5,626,557 A * | 5/1997 | Mann ........................... 602/26 |
| 5,730,710 A | 3/1998 | Eichhorn et al. |
| 5,823,931 A * | 10/1998 | Gilmour ........................ 602/24 |
| 6,287,268 B1 * | 9/2001 | Gilmour ........................ 602/26 |
| 6,589,194 B1 * | 7/2003 | Calderon et al. ........... 601/151 |

FOREIGN PATENT DOCUMENTS

| | | |
|---|---|---|
| EP | 0 670 152 | 9/1995 |
| EP | 0 684 026 | 11/1995 |

* cited by examiner

*Primary Examiner*—Henry Bennett
*Assistant Examiner*—Dinnatia Doster-Greene
(74) *Attorney, Agent, or Firm*—Banner & Witcoff, Ltd.

(57) ABSTRACT

The invention relates to a knee brace with straps engageable with the upper and lower leg and disposed above and below the knee, said straps being connected by a hinged rail extending over the knee at the side, said hinged rail comprising a fluid-inflatable padding and a hinged connection in the region of the knee. The padding comprises two optionally inflatable hollow pads connected by a channel, said hollow pads each being so disposed between the knee-distal straps and the hinged connection that, when the hollow pads are inflated, the knee is forced in relation to the straps into a position away from the hinged connection.

13 Claims, 6 Drawing Sheets

KNEE-JOINT ORTHESIS

The invention relates to a knee brace with straps engageable with the upper and lower leg and disposed above and below the knee, said straps being connected by a hinged rail extending over the knee at the side, said hinged rail comprising a fluid-inflatable padding and a hinged connection in the region of the knee.

BACKGROUND OF THE INVENTION

Such a brace is disclosed in European patent application 670 152 A1. In the known knee brace, an inflatable padding is used to correct the longitudinal axis of the leg, said padding being disposed directly at the side next to the knee and expanding through inflation such as to exert a pressure directly on the knee. Taking into consideration the position of the knee-distal straps placed around the upper leg and lower leg, the hinged rail, which extends laterally over the knee, exerts a moment on the knee, which, depending on the position of the hinged rail on the inside or outside of the leg, is thus brought towards a knock-knee position or bow-legged position. This results in two effects: firstly, a pressure is exerted directly at the side on the knee and therefore on the pain-sensitive joint capsule; secondly, when the knee is bent, the inflatable padding must slide on the skin surrounding the knee, this, of course, being associated with friction and leading, if the brace is worn for lengthy periods of time and especially during sporting activity, to grazing of the corresponding points on the skin.

A further design of knee brace for correcting the longitudinal axis of the leg is disclosed in U.S. Pat. No. 5,302,169. In this. brace, the two arms of a hinged rail extending over upper leg and lower leg are brought by means of adjusting screws into a desired oblique position with respect to a hinged connection consisting in relatively complex manner of two interconnected ball-joint-like sliding bearings.

With this knee brace, it is inevitable that there will be compressive forces acting on the knee, this having a considerably adverse effect on the wearing of such a brace, particularly when the knee is moved. Furthermore, the screw-type adjustment of the two arms of the hinged rail, accomplished via relatively short lever arms, allows a considerable elastic hysteresis of said arms, with the result that the known knee brace cannot be guaranteed to provide a reliable therapeutically required correction of the leg position.

A further knee brace is disclosed in U.S. Pat. No. 4,796,610, in which attached to the end of the arms of a hinged rail are pads which are in contact with the upper and lower leg. Said knee brace is intended to absorb forces occurring transversely with respect to the leg in the region of the knee joint and thereby to prevent injuries of the kind that repeatedly occur especially during the playing of sports. The knee brace serves, therefore, in particular to prevent sports injuries; it is not designed to bring about a conscious correction of the longitudinal axis of the leg.

In addition, it is known, for example, from EP 0 684 026 A1 to provide inflatable pads at the hinged rails of a knee brace for the purpose of padding the hinged rails against the leg, said inflatable pads being able to be individually inflated by the wearer such that the wearing of the knee brace is as convenient as possible, i.e. the pads serve to adapt the hinged rails individually to the form of the respective leg, particularly also to the change thereof during the wearing of the knee brace over the course of a day, in order in this manner to achieve a particularly good fit between the knee brace and the leg.

SUMMARY OF THE INVENTION

The object of the invention is, proceeding from the initially mentioned prior art, to create a knee brace which can be conveniently adjusted by the patient in accordance with his or her individual needs and which permits trouble-free wearing of the knee brace. The object of the invention is achieved, according to a first version, in that the padding comprises two optionally inflatable hollow pads connected by a channel, said hollow pads each being so disposed between the straps and the hinged connection that, when the hollow pads are inflated, the knee is forced in relation to the straps into a position away from the hinged connection.

The object of the invention is achieved, according to a second version, in that the padding comprises two optionally inflatable hollow pads, said hollow pads each being disposed near the knee-proximal straps and away from the hinged connection such that, when the hollow pads are inflated, the upper and lower leg are forced away from the hinged rail.

Depending on the degree of inflation of the hollow pads, it is possible by means of the two optionally inflatable hollow pads to produce a moment through which both the upper leg and also the lower leg can be adjusted in relation to the knee joint at a desired angle with respect to the longitudinal axis of the leg. The occurring pressures are readily absorbed by the respective body parts, because, namely, there are areas on the upper leg and lower leg which are anatomically suited to accepting such forces. In any event, the knee itself remains extensively free from compressive forces, with the result that no pains are able to occur at the knee as a result of the brace itself and the knee is also not subject to any rubbing. The inflatable hollow pads permit a pressure which can be adjusted by the patient him or herself, the patient being readily able him or herself to inflate the hollow pads by means of mouthpieces on the hollow pads and by means of a pump tube with thereto attached hand pump similar to a pump ball, the alleviation of his or her pain helping the patient steplessly to adjust the (for the patient) most advantageous pressure in the hollow pads. Owing to the fact that the two hollow pads are connected by a channel, there is always the same pressure in both hollow pads, even though only one of the two hollow pads is provided with a valve, because, also in this case, there is an equalization of pressure by means of the channel. The fluid used may be a liquid, yet also and in particular a gas, such as air.

In order to stabilize the hinged connection, it is additionally possible to provide a belt extending over the calf side, said belt engaging the side of the knee brace facing away from the hinged connection and being fixable with its free end below the hinged connection. The effect of said belt is that any force acting on the hinged connection upon bending of the knee, said force having the tendency to pull the hinged connection away from the knee, is extensively compensated, with the result that the hinged connection must remain in its necessarily intended position even when the knee is bent.

The inflation of the hollow pads is facilitated in that they are provided with a valve for application of a pump. Such a pump may be a known pump similar to a pump ball of the kind used, for example, in connection with blood-pressure measuring devices.

Depending on whether it is necessary to make a correction more for knock knees or more for bow legs, in the case of the first version the hinged rail is disposed laterally (on the outside) with respect to the knee or medially (on the inside) with respect to the knee or, in the case of the second version, medially or laterally with respect to the knee.

It is advantageous for the knee brace to be in the form of a stocking into which the straps and the hinged rail are embedded or fixed. By being pulled over the leg, a stocking is able to engage the knee in form-fitting manner with particular ease and convenience of use, this additionally resulting in a desirable non-slip characteristic.

The fitting of the knee brace may be facilitated in that, if in the form of a stocking, the knee brace is provided with two shaped pads in the region of the patella, said shaped pads bordering the patella above and below the patella such that any tension in the stocking caused upon bending of the knee is extensively kept away from the patella. Said shaped pads extensively prevent the exertion of a pressure on the patella, because the tension caused upon bending of the knee tautens the stocking from shaped pad to shaped pad without the patella also being affected.

Moreover, the shaped pads serve, when the knee brace is being fitted, to correctly position the knee brace from the outset in relation to the patella, said correct position being felt by the patient when the two shaped pads are in place above and below the patella.

In order to uniformize the pressure exerted by the hollow pads on the upper and lower leg, the hollow pads may advantageously each be covered by a pressure distribution pad adjacent to the upper and lower leg. Such a pressure distribution pad may be made, for example, of a soft silicone rubber. The pressure distribution pads are advantageously fixed in such a manner that they are supported by a carrying plate, said carrying plate being pivotably attached on one side to the hinged rail. Through adjustment of the hollow pads by application thereto of the appropriate pressure it is possible for the carrying plate to be adjusted at a slight angle with the pressure distribution pad and thus for it to adapt to the desired angled position of the upper leg in relation to the lower leg.

The hinged rail is particularly suitable for the attachment of the hollow pads, the hollow pads in this case being attached to the hinged rail adjacent to the upper leg and lower leg, for example by means of glueing. Alternatively, it is possible for the hollow pads to be attached to the carrying plate.

In order to provide the hollow pads with a suitable counter-bearing, it is advantageous to provide supporting plates, said supporting plates covering the hollow pads and each being attached to a hinged rail.

BRIEF DESCRIPTION OF THE DRAWINGS

Example embodiments of the invention are presented in the drawings, in which.

DETAILED DESCRIPTION OF THE INVENTION

Figure 1:
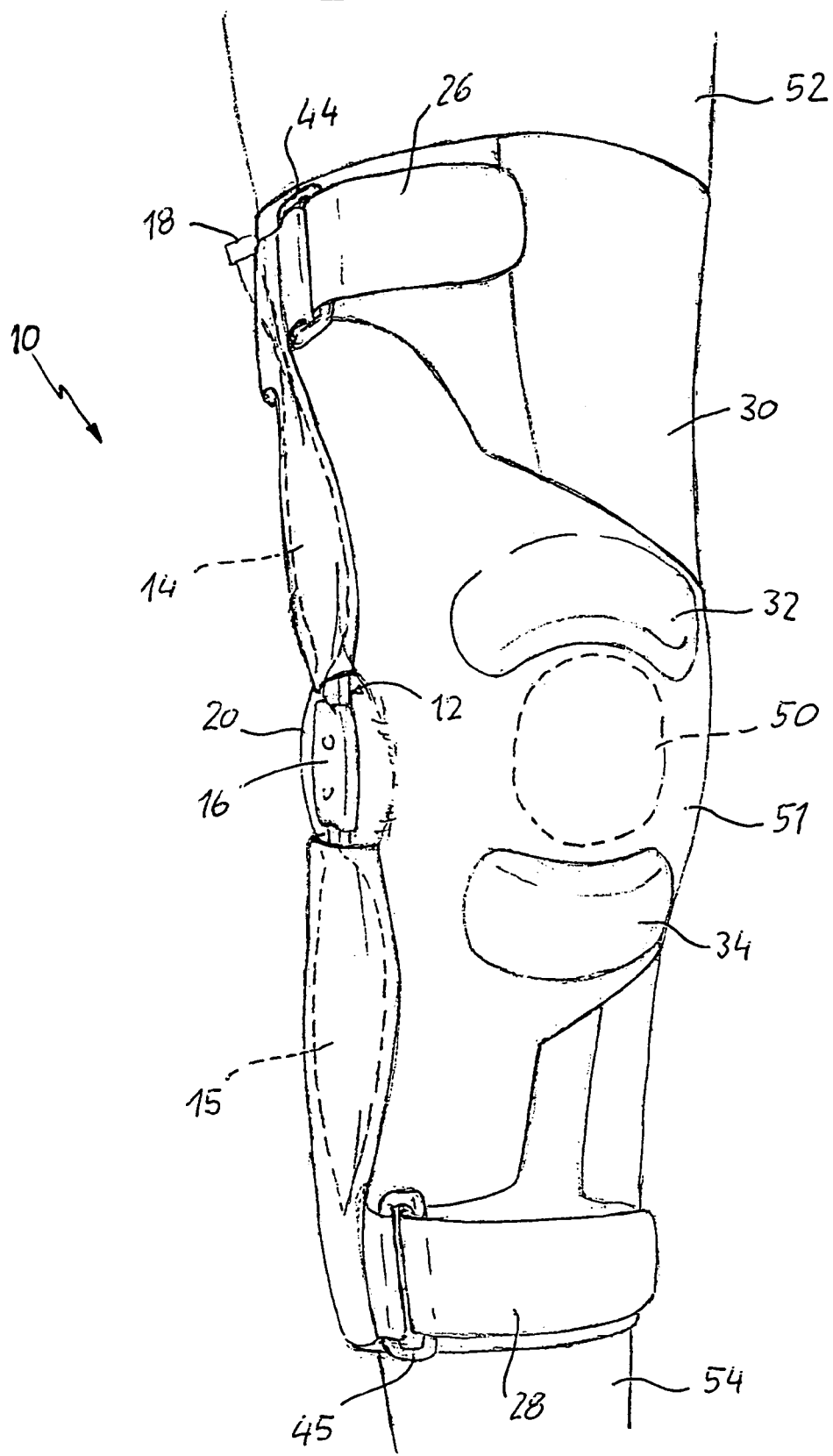
FIG. 1 shows the knee brace according to the first version in a perspective view and fitted laterally to a right leg.

FIG. 1 shows a knee brace 10 of the first version, fitted to the upper leg 52 and lower leg 54, said knee brace 10 containing the stocking 30, said stocking 30 having been pulled over the knee 51, the position of the knee 51 being described by the patella 50 drawn with a dashed line. The knee brace 10 is tightened around the upper leg 52 by the strap 26 and around the lower leg 54 by the strap 28. The knee brace 10 is thus extensively fixed in relation to its position with respect to the upper leg 52 and lower leg 54.

Figure 2:
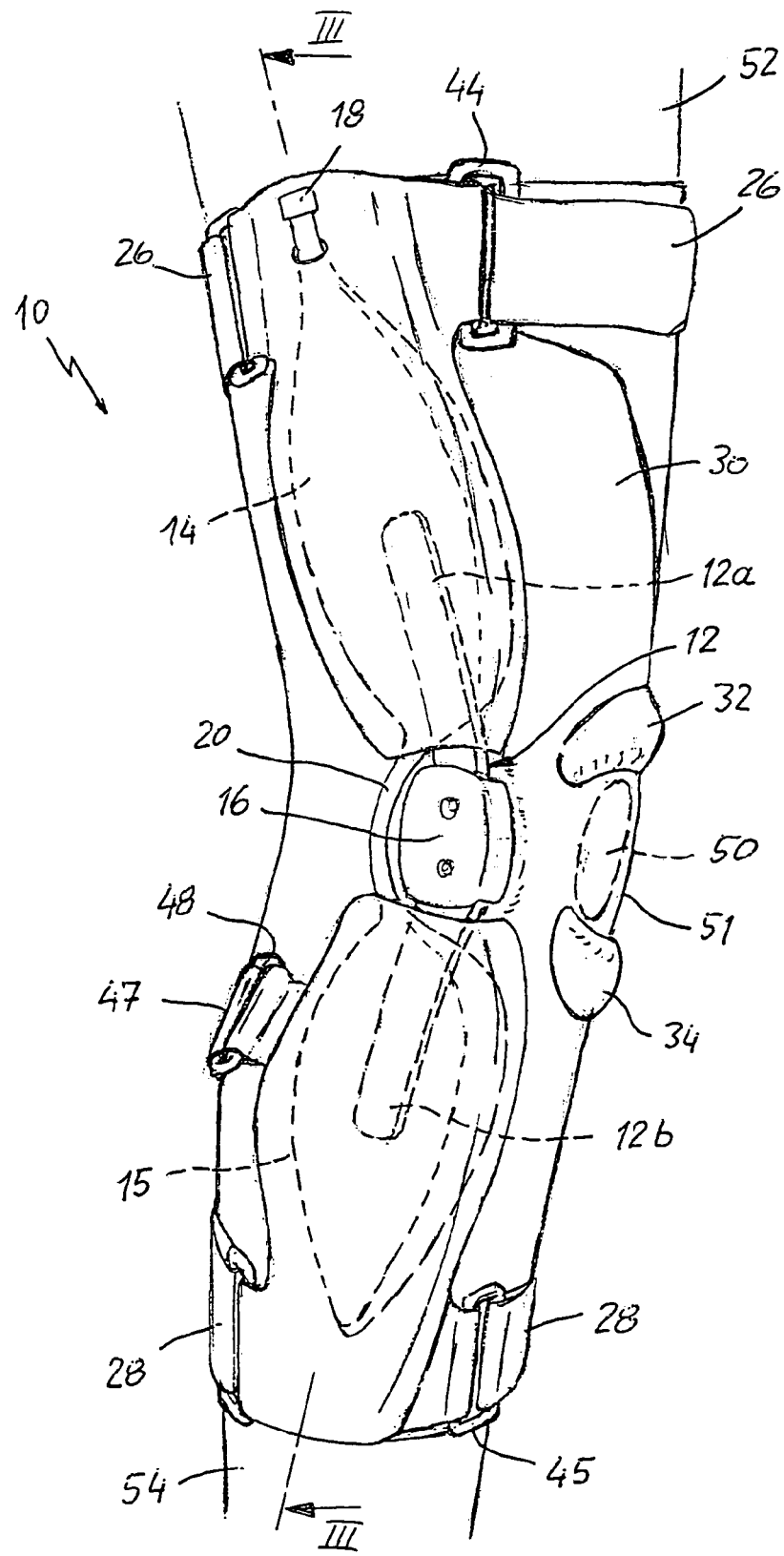
FIG. 2 shows the same knee brace in a side view.

The above-named parts of the knee brace 10 are likewise presented in FIG. 2, which shows the knee brace in a side view, more specifically in a side view of the lateral side of a right knee. Incorporated into the knee brace 10 is the hinged rail 12a/12b, which extends with its arm 12a over a portion of the upper leg 52 and with its arm 12b over a portion of the lower leg 54 and which has the hinged connection 16 in the region of the knee 51. Owing to the hinged connection 16, the hinged rail 12a/12b is able to bend in conformance with the movement of the upper leg 52 and lower leg 54.

The hinged rail 12a/12b comprises an inflatable padding, consisting of the hollow pad 14 and the hollow pad 15, which are each disposed between the knee-distal straps 26 and 28 and the hinged connection 16. The hollow pads 14 and 15 are inflated by means of the valve 18, through which air can be blown into the hollow pads 14 and 15 in known manner, as will be discussed in fuller detail hereinbelow.

For this purpose, a pump is connected to the valve 18, such pump being, for example, a pump ball of the kind used in connection with blood-pressure measuring devices.

The inflation of the hollow pads 14 and 15 results in a pressure on that region of the upper leg 52/lower leg 54 which is situated between the straps 26/28 and the hinged connection 16, as a result of which the knee 51 is forced from the hinged connection 16 towards the other knee, i.e. towards a knock-knee position, because the hinged rail 12a/12b remains extensively rigid in relation to the forces acting on it.

This forcing away of the knee 51 from the hinged connection 16 results, therefore, in the desired therapeutic effect whereby, in the respective leg of the patient, the knee 51 is brought into a position closer to a knock-knee position.

It should additionally be pointed out that the fixing of the straps 26 and 28 is accomplished in known manner by wrapping around the upper leg 52 and lower leg 54, the respective ends of the straps 26, 28 then being pulled through the buckles 44 and 45 and thereafter being fixed in known manner to the leg-encompassing parts of the straps 26 and 28 by means of hook-and-pile fasteners.

In the region of the knee 51, the stocking 30 is provided with the two shaped pads 32 and 34, which surround the patella 50 above and below said patella 50 (indicated by the dashed line). The shaped pads 32 and 34 may be, for example, silicone pads which are inserted into the stocking 30. On the one hand, the shaped pads facilitate the fitting of the knee brace to the extent that the patient can feel when the region of his or her patella comes between the shaped pads 32 and 34. On the other hand, the shaped pads 32 and 34 ensure that, upon bending of the knee 51, the material of the stocking 30 in the region of the knee 51 is not able to become taut directly above the patella 50, because, namely, the shaped pads 32 and 34 keep the material of the stocking extensively away from the region of the patella 50.

Figure 3:
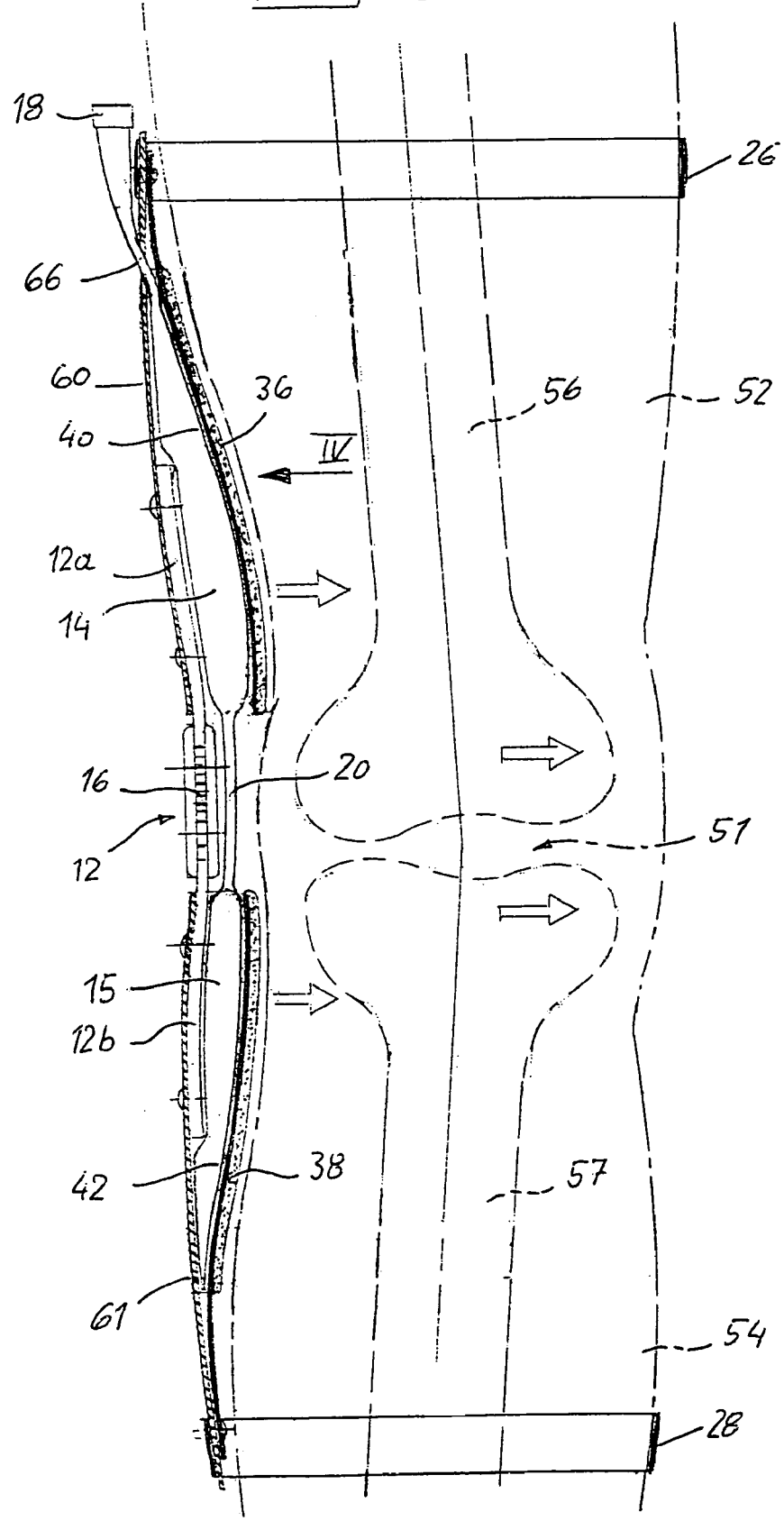
FIG. 3 shows the same knee brace in section along line III—III from FIG. 2.

FIG. 3 shows a longitudinal section through-the knee brace 10 according to FIGS. 1 and 2 (see section line III—III in FIG. 2), indicating the knee 51, the thigh-bone 56 and the tibia 57, as well as the straps 26 and 28, wherein the buckles 44 and 45 have been omitted for the purpose of simplification of the representation. Furthermore, the stocking identified by reference character 30 in FIGS. 1 and 2 is not included in the drawing, in order thus to clearly illustrate the design of the hinged rail 12a/12b with its associated components.

Shown originating from the hinged connection 16 is the hinged rail 12a/12b, which extends from the hinged connection 16 both towards the upper leg 52 and also towards the lower leg 54. Riveted onto the hinged rail 12a/12b is the upper supporting plate 60 and the lower supporting plate 61, which each cover a hollow pad, these being more specifically the hollow pad 14 in the region of the upper leg 52 and the hollow pad 15 in the region of the lower leg 54. FIG. 3 shows the hollow pads 14 and 15 in the inflated position in which they force the knee-proximal portions of the upper leg 52 and lower leg 54 away from the hinged connection 16, thereby forcing the respective leg of the patient more into a knock-knee position. The two hollow pads 14 and 15 are inflated by means of the valve 18 and the tube 66, which joins into the hollow pad 14, as well as by means of the channel 20, which connects the hollow pad 14 to the hollow pad 15. In this manner, the two hollow pads 14 and 15 are simultaneously inflated by means of the valve 18. On one side, the hollow pads 14 and 15 are supported against the supporting plates 60 and 61 while, on the other side, the hollow pads 14 and 15 press against the carrying plates 40 and 42 and, through the intermediary thereof, on the pressure distribution pads 36 and 38, as a result of which the latter ensure that there is no locally excessive pressure in relation to the upper leg 52 and lower leg 54.

Figure 4:
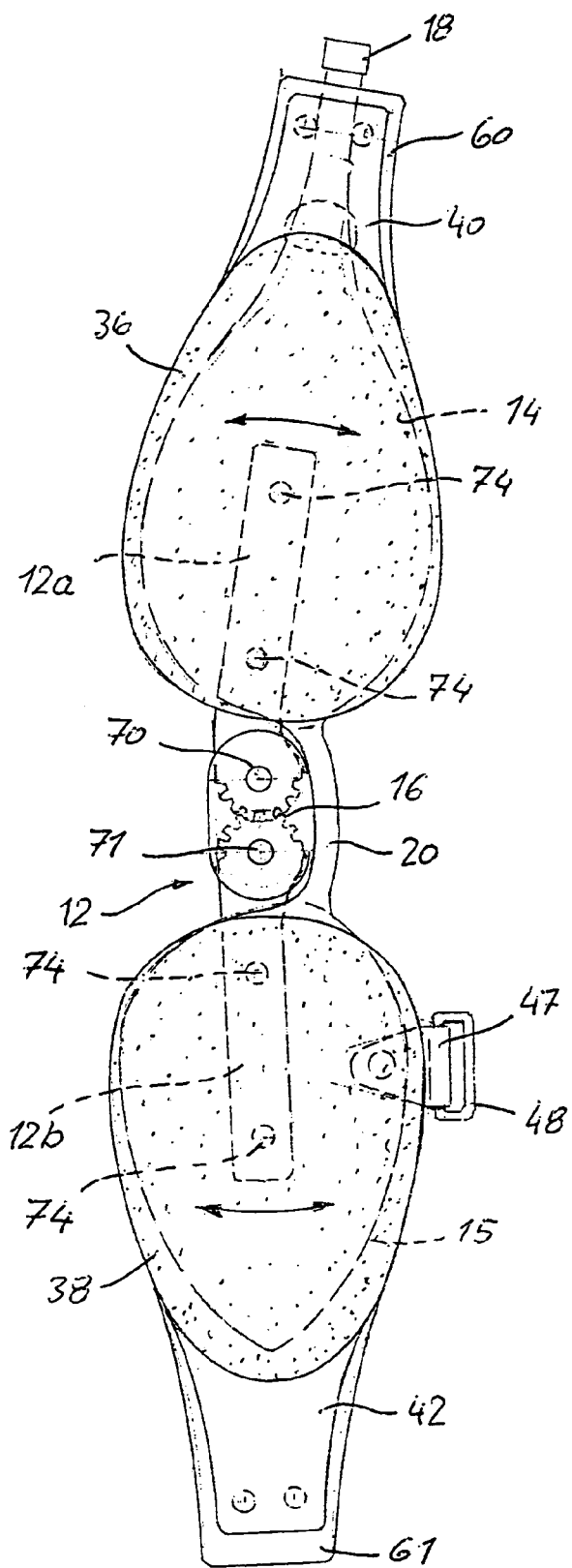
FIG. 4 shows the hinged rail of the embodiment according to FIG. 1 to 3 in a view of the side facing the leg.

FIG. 4 shows separately those components which are directly connected to the hinged rail 12a/12b, this being in order especially to illustrate the operating principle of those components. FIG. 4 shows the hinged connection 16, which contains he two shafts 70, 71 on which are located the two arms of the hinged rail 12a/12b. Said two arms each terminate in a toothed section, the two toothed sections of the two arms intermeshing, with the result that, upon bending of the knee and thus of the two arms of the hinged rail 12a/12b, there is a rolling contact in the region of the toothed sections. This type of mutually induced movement of the two arms of the hinged rail 12a/12b via the two shafts 70 and 71 with the two toothed sections is extensively adapted in known manner to the articulated movement of the human knee. The two arms 12a and 12b are permanently connected via the rivets 74 to the two supporting plates 60 and 61, which completely cover the above-lying hollow pads 14, 15, with the result that the hollow pads 14 and 15 are well supported in relation to the supporting plates 60 and 61. When the hollow pads 14 and 15 are inflated, they push the carrying plates 40 and 42 in front of them, as it were, and thus force the pressure distribution pads 36 and 38 away from the supporting plates 60 and 61, as a consequence of which the pressure presented in connection with FIG. 3 is exerted on the upper leg 52 and lower leg 54.

Figure 5:
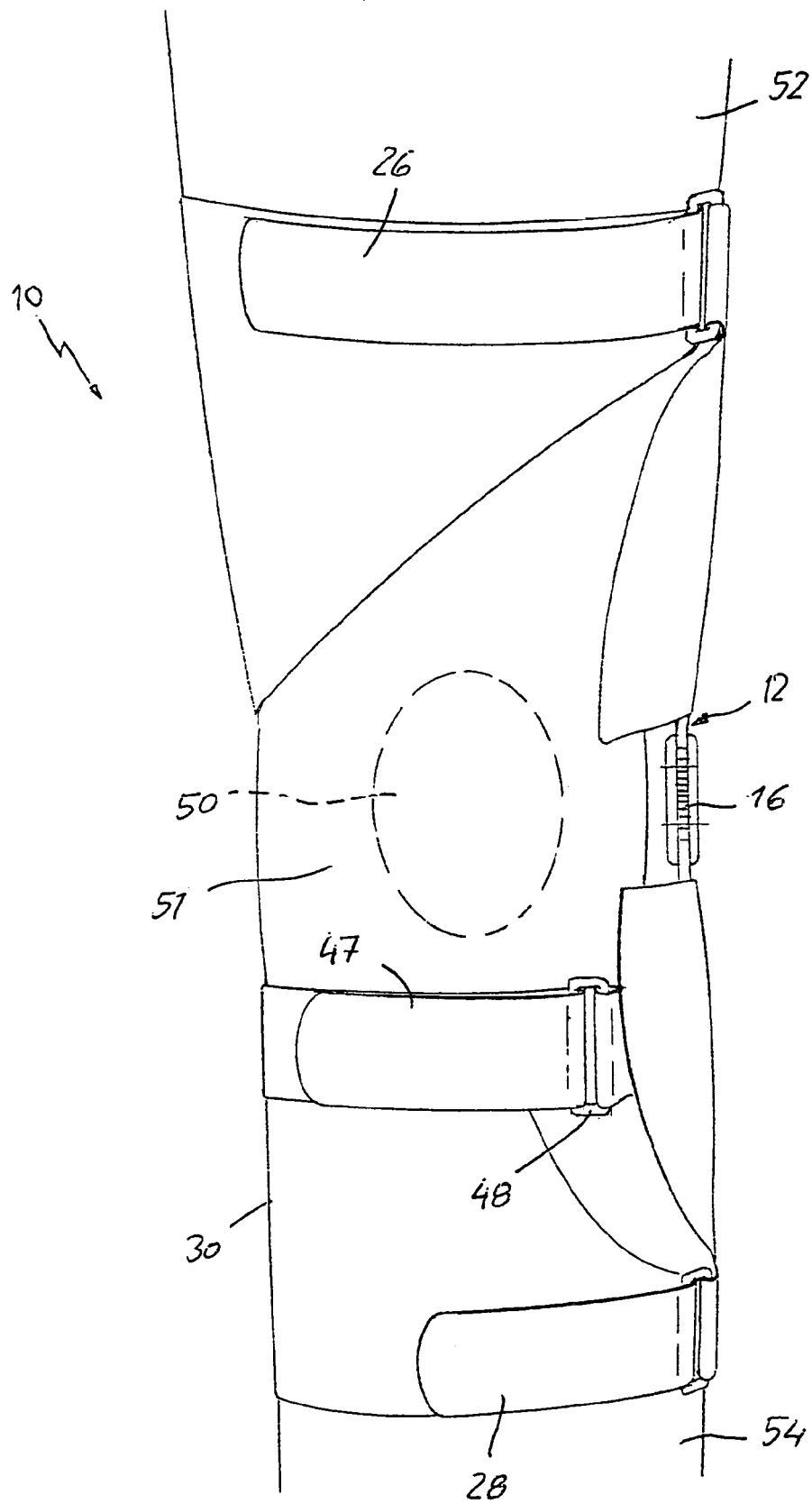
FIG. 5 shows the same knee brace in a view of the hollow of the knee.

FIGS. 2, 4 and 5 show a further component of the knee brace according to the invention, said component consisting of a belt 47, said belt 47 starting on the side of the knee brace facing away from the hinged connection 16, i.e. on the opposite side of the knee brace, extending over the calf side and being fixable with its free end to the stocking 30 below the hinged connection 16. As is apparent from FIGS. 4 and 5, the belt 47 is connected to the buckle 48, through which buckle 48 the belt 47 is looped and which buckle 48 is fixable to the stocking 30 in the region below the hollow of the knee. This is accomplished in known manner by means of a hook-and-pile fastener. Through said belt 47 the hinged connection 16 is subjected to a tensile force via the calf side from the region below the hollow of the knee when the knee joint 51 is bent. When this happens, namely, the hinged connection 16 has the tendency to move towards the patella 50, this being prevented by the belt 47. Said belt, therefore, provides the knee brace with a special inner stability.

As shown in the representations in the above-discussed FIG. 1 to 5, the hinged rail 12a/12b is situated, as stated, on the lateral side of a right knee joint, as a consequence of which, when the hollow pads 14 and 15 are inflated, the respective leg of the patient is forced into a position tending towards a knock-knee position. The opposite effect upon extension of the knee can be achieved in that the knee brace is fitted on the medial side of the patient's leg, this then, conversely, giving the leg in question the tendency towards a bow-legged position.

Figure 6:
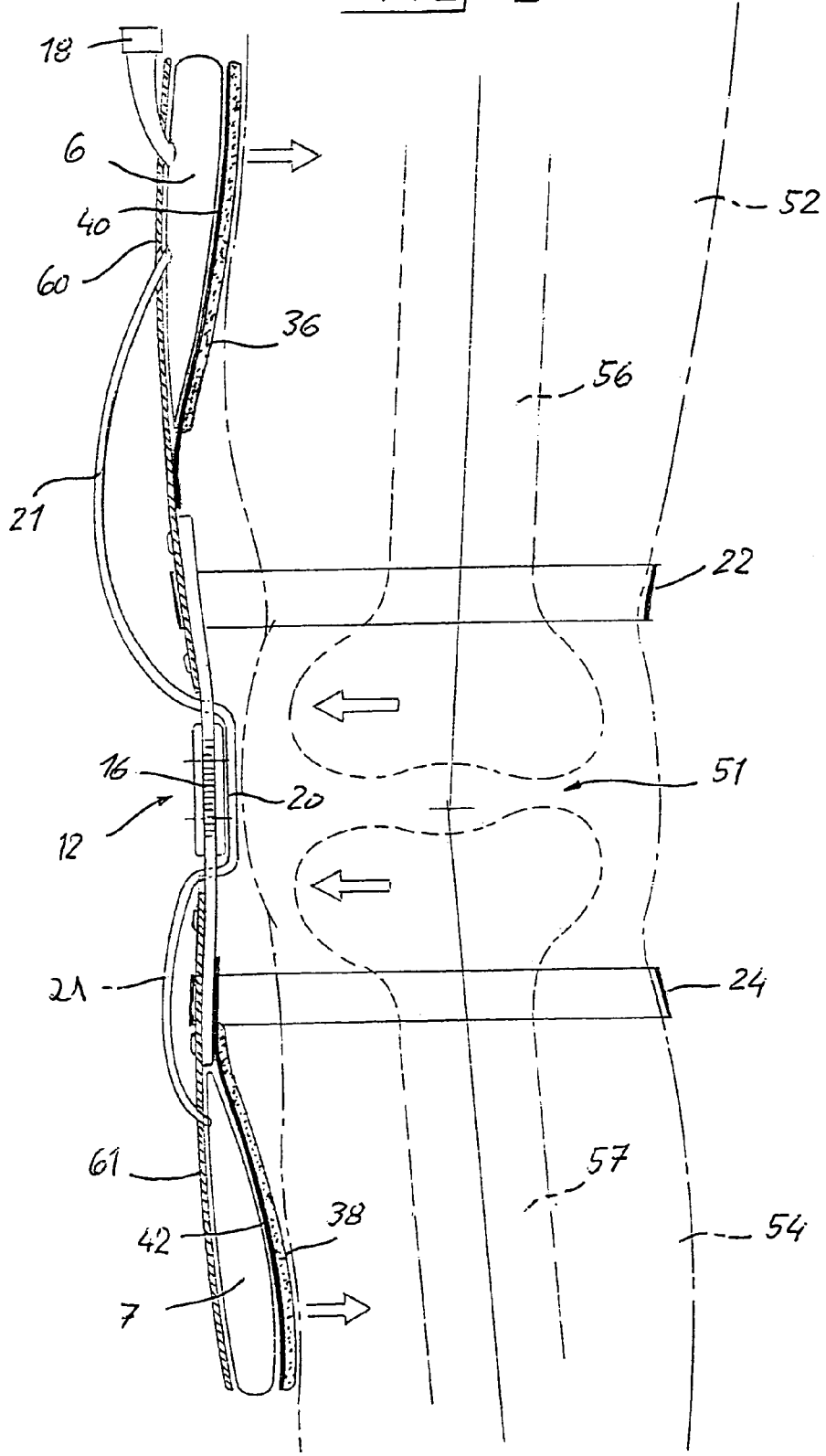
FIG. 6 shows a knee brace according to the second version in section.

FIG. 6 shows a further possibility for producing a bow-legged position. Once again, the knee brace is fitted laterally to a right leg. In this knee brace, the hollow pads 6 and 7 are in a position further away from the knee 51, the straps 22 and 24 being additionally provided near the knee 51. As viewed from the knee 51, therefore, the hollow pads 6 and 7 are situated outside the region of the straps 22 and 24. As in the knee brace according to FIG. 3, the hollow pads 6 and 7 are disposed between the supporting plates 60 and 61 as well as between the carrying plates 40 and 42, with the result that, when the hollow pads 6 and 7 are inflated by means of the valve 18, the carrying plates 40 and 42 are forced away from the supporting plates 60 and 61, the pressure being transmitted to the upper leg 52 and lower leg 54 via the pressure distribution pads 36 and 38. Inasmuch, this operating principle is the same as that described with reference to FIG. 3.

In this case, the connection between the hollow pad 6 and the hollow pad 7 is accomplished by means of the channel 21, through which the air pumped into the hollow pad 6 is able to flow across into the hollow pad 7, with the result that, finally, there is the same pressure in both hollow pads. The opposite effect upon extension of the knee can be achieved in that the knee brace is fitted on the medial side of the patient's leg, this then, conversely, giving the leg in question the tendency towards a knock-knee position.

What is claimed is:

1. Knee brace with straps engageable with the upper and lower leg and dispositional above and below the knee, said straps being connected by a hinged rail for extending over a side of the knee, said hinged rail comprising a fluid-inflatable padding and a hinged connection for positioning in the region of the knee, wherein the padding comprises two optionally inflatable hollow pads connected by a channel, said hollow pads each being so disposed between the knee-distal straps and the hinged connection that, when the hollow pads are inflated, the knee is forced in relation to the straps into a position away from the hinged connection.

2. Knee brace for making a correction to the knee, said brace comprising a first side, a second side, and straps engageable with the upper and lower leg and dispositional above and below the knee, said straps being connected by a hinged rail extending along said first side, said hinged rail for extending over a side of the knee, and comprising a fluid-inflatable padding and a hinged connection for positioning in the region of the knee, wherein the padding comprises two optionally inflatable hollow pads, said hollow pads each being disposed near the knee-proximal straps, said straps being positioned between said pads and the hinged connection such that, when the hollow pads are inflated, the upper and lower leg are forced away from the hinged rail in a direction of said second side that is free of inflatable padding.

3. Knee brace according to claim 1, wherein the side thereof facing away from the hinged connection is engaged by a belt extending over the calf side, said belt being fixable with its free end below the hinged connection.

4. Knee brace according to claim 1, wherein at least one hollow pad is provided with a valve for application of a pump.

5. Knee brace according to claim 1, wherein the hinged rail is disposed laterally with respect to the knee.

6. Knee brace according to claim 1, wherein the hinged rail is disposed medially with respect to the knee.

7. Knee brace according to claim 1, wherein the straps and the hinged rail are embedded in a stocking.

8. Knee brace according to claim 7, wherein the stocking comprises two shaped pads in the region of the patella, said shaped pads bordering the patella above and below the patella such that any tension in the stocking caused upon bending of the knee is extensively kept away from the patella.

9. Knee brace according to claim 1, wherein the hollow pads are each covered by a pressure distribution pad adjacent to the upper and lower leg.

10. Knee brace according to claim 9, wherein each pressure distribution pad is supported by a carrying plate, said carrying plate being pivotably attached on one side to the hinged rail.

11. Knee brace according to claim 1, wherein the hollow pads are attached to the hinged rail.

12. Knee brace according to claim 10, wherein the hollow pads are each attached to the carrying plate.

13. Knee brace according to claim 1, wherein the hollow pads are each covered by a supporting plate attached to the hinged rail.

* * * * *